United States Patent [19]

Leagre et al.

[11] Patent Number: 5,404,873
[45] Date of Patent: Apr. 11, 1995

[54] ANESTHESIA CIRCUIT

[75] Inventors: Michael A. Leagre, Fishers; Kevin D. Burrow, Carmel, both of Ind.

[73] Assignee: King System Corporation Division of Barco Molding, Inc., Noblesville, Ind.

[21] Appl. No.: 77,729

[22] Filed: Jun. 16, 1993

[51] Int. Cl.$^6$ ............... A61M 16/00; A62B 7/00; A62B 18/02

[52] U.S. Cl. ............ 128/204.18; 128/205.25; 128/203.29; 128/912; 128/DIG. 26; 128/205.13

[58] Field of Search ............ 128/911, 912, 207.14, 128/206.21, 204.18, 205.13, 205.25, DIG. 26, 203.12, 203.29

[56] References Cited

U.S. PATENT DOCUMENTS

| | | | |
|---|---|---|---|
| 746,380 | 12/1903 | Richardson et al. | 128/203.25 |
| 3,881,482 | 5/1975 | Lindholm | 128/201.13 |
| 3,889,671 | 6/1975 | Baker | 128/207.13 |
| 4,007,737 | 2/1977 | Paluch | 128/201.13 |
| 4,200,094 | 4/1980 | Gedeon et al. | 128/201.13 |
| 4,265,235 | 5/1981 | Fukunaga | 128/200.24 |
| 4,281,652 | 8/1981 | Miller | 128/204.25 |
| 4,320,754 | 3/1982 | Watson et al. | 128/204.25 |
| 4,430,994 | 2/1984 | Clawson et al. | 128/203.27 |
| 4,440,163 | 4/1984 | Spergel | 128/205.13 |
| 4,463,755 | 8/1984 | Suzuki | 128/204.18 |
| 4,521,038 | 6/1985 | Cerny | 285/24 |
| 4,637,384 | 1/1987 | Schroeder | 128/204.18 |
| 4,676,239 | 6/1987 | Humphrey | 128/205.17 |
| 4,682,010 | 7/1987 | Drapeau | 219/381 |
| 4,686,354 | 11/1987 | Makin | 219/301 |
| 4,825,859 | 5/1989 | Lambert | 128/202.16 |
| 5,140,983 | 8/1992 | Jinotti | 128/207.14 |
| 5,176,150 | 1/1993 | Hartwig | 128/773 |
| 5,284,160 | 2/1994 | Dryden | 128/203.12 |

FOREIGN PATENT DOCUMENTS 2025239 1/1980 United Kingdom ............ 128/911

*Primary Examiner*—Kimberly L. Asher
*Attorney, Agent, or Firm*—Bose McKinney & Evans

[57] ABSTRACT

A breathing circuit is provided for conveying an inspiratory gas from a gas dispensing apparatus to a patient, and for conveying an expiratory gas from the patient. The circuit includes a corrugated expiratory tube having a first end and a second end. The expiratory tube has a relaxed length. A corrugated inspiratory tube is provided which is disposed generally colinearly and interiorly of the expiratory tube. The inspiratory tube has a first end disposed adjacent to the first end of the expiratory tube, a second end disposed adjacent to the second end of the expiratory tube, and a relaxed length greater than the relaxed length of the expiratory tube such that the inspiratory tube normally exerts a longitudinally directed pressure on the circuit. A first end coupling member is fixedly coupled to both the inspiratory tube and the expiratory tube. The first end coupling member is generally transparent and hollow, and has an interior and an exterior. The first end coupling member is generally more rigid than the expiratory tube. A second end coupling member is fixedly attachable to the second end of the expiratory tube. The second end coupling member includes a positioning member receiving portion. A positioning member for positioning the second end of the inspiratory tube relative to the positioning end receiving portion of the second end coupling member is also provided.

17 Claims, 5 Drawing Sheets

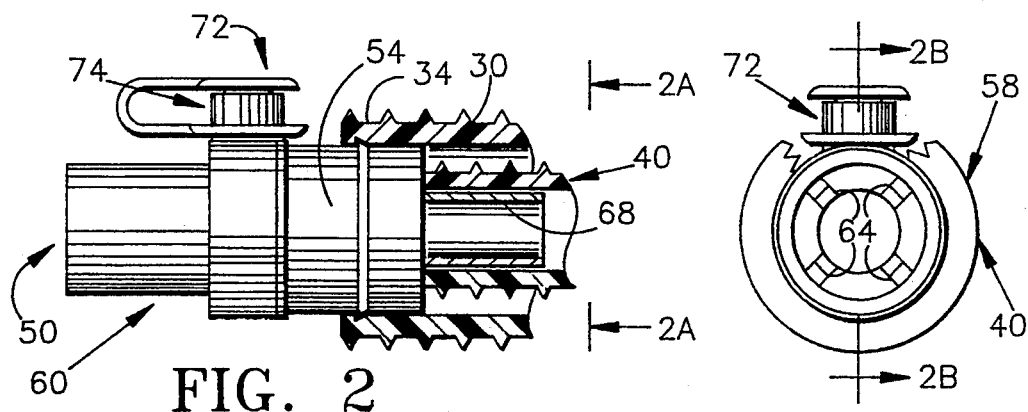
FIG. 2
FIG. 2A
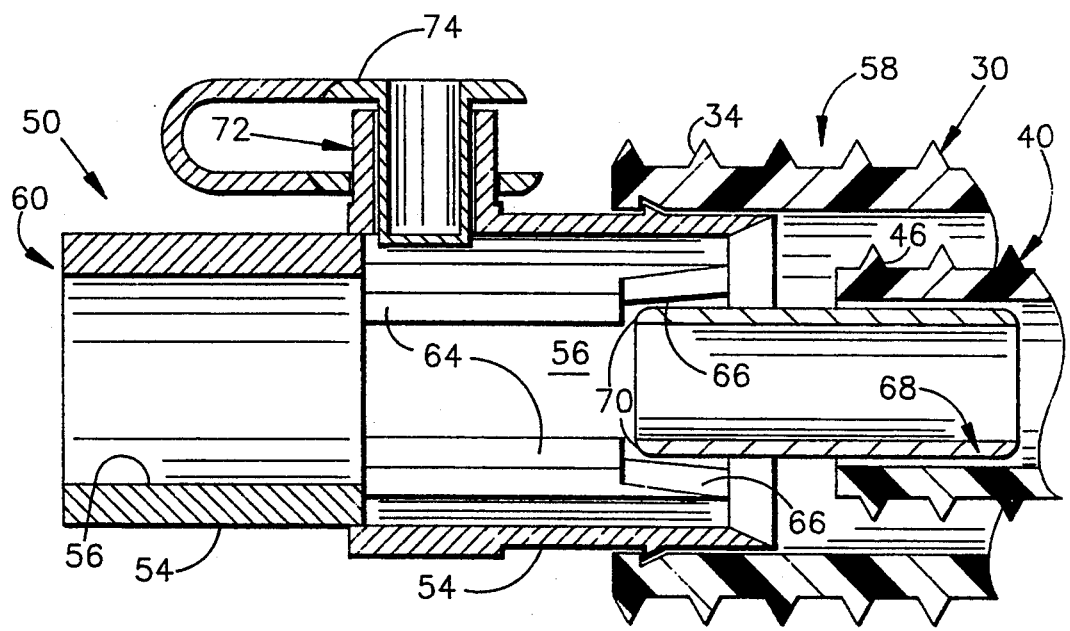
FIG. 2B
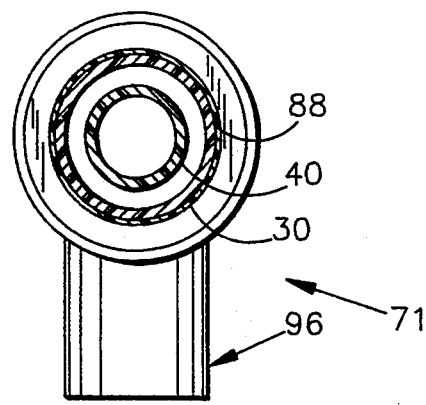
FIG. 3A

ANESTHESIA CIRCUIT

I. TECHNICAL FIELD OF THE INVENTION

The present invention relates to medical devices, and more particularly, to a breathing circuit adapted for use in connection with conveying an inspiratory gas (such as oxygen or an anesthetic) from a gas dispensing apparatus to a patient, and conveying expiratory gases from the patient.

II. BACKGROUND OF THE INVENTION

For years, medical science has administered various gases to patients. Primarily these gases include anesthetics that are administered to patients during surgery, and oxygen or air that is administered to patients either post-operatively, or at other times for therapeutic reasons.

The gas to be administered is typically contained within a sealed container. The sealed container includes an outlet port and a valve for controlling the flow of gas through the outlet port. A breathing circuit is provided for transporting the gas from the outlet port to an element such as a face mask that is in contact with a patient.

Various types of breathing apparatus and circuits have been used in the past.

Richardson and Field U.S. Pat. No. 746,380 discloses a device that was patented in 1903 for administering anesthetics. The Richardson device includes a mouth part and a nose part. The mouth and nose parts are separately connected by means of a bushing or tubular fitting. The device includes a gas receptacle which has a flexible tube at one end, and is secured in place by an elastic band or strap.

A more recent prior art breathing circuit is shown in FIGS. 1 and 2 of Fukunaga U.S. Pat. No. 4,265,235. This illustrated device comprises a typical "circle-type" breathing circuit that includes a source of gas, a conduit extending therefrom, and a carbon dioxide absorber which receives expiratory gas through a conduit. Reprocessed gas moves out of the outlet after having passed through the carbon dioxide absorbing granules. As the reprocessed gas moves out of the outlet, it joins fresh gas from the source, as the fresh gas is arriving through the conduit. The merged gases then pass through the one-way inspiratory valve and the flexible hose into the common inlet-outlet pipe as inspiratory gas to the inlet means, and then to the patient's respiratory system. The expiratory gas is returned through the inlet pipe, but is then passed through the return hose, a one-way expiratory valve, past a reservoir bag and into the carbon dioxide absorber.

One difficulty with circle-type devices such as the prior art device shown in FIGS. 1 and 2 of Fukunaga is that they are cumbersome and inefficient. To overcome the problems of such circle-type systems, UNILIMB systems have been developed wherein an inspiratory tube and an expiratory tube have been designed to be coaxial with each other, so that one (usually the inspiratory tube) fits inside the other (usually the expiratory tube). With such an arrangement, manipulation becomes less complicated, and the surgical theater becomes less cluttered as the anesthesiologist has one less breathing tube to deal with. Examples of such UNILIMB type circuits are shown in Fukunaga U.S. Pat. No. 4,265,235 and Paluch U.S. Pat. No. 4,007,737.

Paluch discloses an anesthesia breathing apparatus which includes concentrically oriented double tubular inhalation and exhalation lines, having one of the tubes positioned interiorly of the other tube. In Paluch, the inhalation (inspiratory) tube is the corrugated inner tube, and the corrugated exhalation (expiratory) tube is disposed exteriorly of the inhalation tube. A fitting is provided at the machine end of the tube and another fitting is provided at the patient end of the device. A face mask is coupled to the fitting at the patient end of the device.

Fukunaga relates to an anesthesia system breathing circuit of the coaxial type. Fukunaga's device includes an inspiratory tube which is disposed interiorly of the expiratory tube. The difference of the diameter of these two tubes is such that a sufficient volume of expiratory air may pass between the outer wall of the inspiratory tube and the inner wall of the expiratory tube. In the Fukunaga device, the outer tube is preferably constructed as a corrugated tube, while the inner tube is preferably extruded of a vinyl type smooth bore material. A first terminal element is provided at one end of the tubes, and a second terminal element is provided at the other end of the tubes.

Although the above discussed devices most likely perform their intended function in a workman-like manner, room for improvement exists. It is therefore one object of the present invention to provide a breathing circuit which improves upon the known coaxial-type breathing circuits by eliminating some of the problems and drawbacks found with prior, known coaxial-type breathing circuit systems.

III. SUMMARY OF THE INVENTION

In accordance with the present invention, an anesthesia circuit is provided for conveying an inspiratory gas from a gas dispensing apparatus to a patient, and for carrying an expiratory gas from the patient. The circuit comprises a corrugated expiratory tube having a first end and a second end. A corrugated inspiratory tube is disposed generally colinearly and interiorly of the expiratory tube. The inspiratory tube has a first end disposed adjacent to the first end of the expiratory tube, and a second end disposed adjacent to the second end of the expiratory tube. A substantially rigid second end coupling member is fixedly attached to the second end of the expiratory tube. A positioning member is fixedly attachable to the second end of the inspiratory tube for positioning the inspiratory tube relative to the second end coupling member. The positioning member is relatively more rigid than the inspiratory tube member.

Preferably, the second end coupling member includes a positioning member receiving portion for freely, slidably receiving the matable positioning member of the inspiratory tube to permit relative longitudinal movement of the inspiratory tube member and the expiratory tube member. The inspiratory tube has a greater relaxed length than the relaxed length of the expiratory tube, to permit the inspiratory tube to normally exert longitudinally directed pressure against the expiratory tube.

Also, in a preferred embodiment, the device includes a transparent, generally hollow first end coupling member having an interior and exterior, and being more rigid than the expiratory tube member. The first end coupling member includes: a first connector port for engaging the first end of the expiratory tube; a second connector port disposed generally colinearly, and adjacent to the first end of the inspiratory tube; and a third connector port in fluid communication with the first end of the expiratory tube. The first end member is sized and configured for also receiving a breathing bag means (of the type normally used with an anesthesia machine) and a breathing bag connector.

Also in accordance with the present invention, in a method for manufacturing an anesthesia circuit for conveying an inspiratory gas from a gas dispensing apparatus to a patient, and for conveying an expiratory gas from the patient, a process is provided for manufacturing a first end coupling member which is capable of being fixedly coupled to the first ends of each of the expiratory tube member and the inspiratory tube member is disclosed. The process comprises the steps of molding a first portion of the first-end coupling member to include a first connector port for engaging the first end of the expiratory tube, a third connector port in fluid communication with the interior of the first end of the expiratory tube, and a rim portion. A second portion of the first-end coupling member is molded to include: a second connector port disposed generally colinearly with, and adjacent to the first end of the inspiratory tube; an inspiratory tube connector flange to which the first end of the inspiratory tube is coupled; and a first portion connector flange mateable with and bondable to the rim of the first portion for joining together the first portion and the second portion. The first end of the inspiratory tube is fixedly coupled to the inspiratory tube connector flange. The inspiratory tube is passed through the first connector port of the first portion. The first and second portions are then joined together by engaging the rim of the first portion to the first portion connector flange of the second portion. The first and second portions are permanently bonded together at the intersection of the rim and the first connector flange of the second portion.

One feature of the present invention is that a positioning member is provided on the end of the inspiratory tube. This feature has the advantage of permitting the use of a freely moveable, non-connected end of the inspiratory tube (or the entire circuit), while ensuring that after the occurrence of movement of the end of the inspiratory tube (or the entire circuit), the inspiratory tube will return to its proper placement relative to the expiratory tube, so that anatomical dead space at the patent end of the circuit is minimized. This characteristic of minimizing dead space is generally recognized within the industry as a benefit to the end user. It has been found by the applicant that during use, a breathing circuit is often pulled and distorted while being positioned, so that the inspiratory tube and expiratory tube are stretched. As in the case of a co-axial type circuit, the expiratory tube is disposed exteriorly of the inspiratory tube. A normal occurrence is that the anesthesiologist or nurse grabs the circuit and pulls it, during which time the inspiratory tube is not grabbed and remains essentially in its original place. When this occurs, the relative longitudinal position of the respective ends of the inspiratory tube and the expiratory tube will change. The positioning means provided by the present invention permits the end of the inspiratory tube to be freely moveable relative to the expiratory tube, so as to permit this movement without breaking the fluid communication between the gas dispensing apparatus and the "machine end" of the inspiratory tube. When the expiratory tube is later released so that it can return to its "relaxed" position, the positioning member of the inspiratory tube will tend to cause the patient end of the inspiratory tube to return to its proper nesting position adjacent to the end of the expiratory tube. This "adjacent to the end" positioning is considered preferable for ensuring a proper bi-directional flow of gases.

It is also a feature of the present invention that the device uses an inspiratory tube which is corrugated along its entire length. The use of a corrugated inspiratory tube has two advantages. The first advantage is that the use of the corrugated inspiratory tube better permits the circuit to be positioned properly by creating a spring-like effect at the patient end of the circuit and also better permits the inspiratory tube to respond to changes in the length of the circuit tube induced by pulling or pushing of the tube during an operation. This response is achieved without compromising the supply of fresh gas delivered to the patient. The second advantage of the corrugated tube is that it makes the device more resistant to damage during handling of the device, and during shipment. It has been found by applicants that non-corrugated inspiratory tubes are subject to kinking and other damage during handling and shipment. A corrugated inspiratory tube is less likely to be kinked, or otherwise malfunction (restrict gas flow) as a result of damage which occurred during handling or shipment of the device.

A further feature of the present invention is that a first-end coupling member and a breathing bag connector are provided which are designed to be coupled to each other, and also to an anesthesia breathing bag. This feature has the advantage of enabling the breathing circuit to be coupled to an anesthetic dispensing apparatus, and be used as an anesthesia circuit during an operation or at such other time during which anesthesia is being administered to a patient, and also to be used as an oxygen supply breathing circuit which can be transported with the patient as he/she is moved from the operating room to other areas of the hospital (such as the recovery room) for post-operative treatment. By enabling the same breathing circuit to be used both during an operation and also thereafter, the need for a second circuit is eliminated. Thus, the time labor and expense associated with the second circuit is eliminated.

An additional feature of the present invention is that the first-end coupling member is manufactured through a process wherein the first and second portions of the end coupling are formed separately, the inspiratory tube is fixedly coupled to the second portion, and the first portion is slid over the inspiratory tube. Finally, the first portion is joined to the second portion in an air-tight relation. This manufacturing technique has the advantage of facilitating the formation of a permanent bond between the inspiratory tube and the first connector which helps to prevent the inspiratory tube from becoming disconnected. As will be appreciated by those familiar with the art, it is most important to avoid a situation during surgery wherein an inspiratory tube becomes disconnected from a breathing circuit connector at the machine end of the device. Such a disconnection often causes an undesirable (and possibly dangerous) increase in "dead space", and inhibits the administration of anesthetic to the patient, and the conveyance of the exhaust gas away from the patient. Another advantage achieved by the Applicants' first end coupling is that it provides a chamber in which bi-directional gas flows are separated, yet encompassed by a single housing.

These and other features and advantages of the present invention will be apparent to those skilled in the art upon reviewing the detailed description of the preferred embodiment disclosed below which represents the best mode known to applicant currently of practicing the present invention.

IV. BRIEF DESCRIPTION OF THE DRAWINGS

FIG. 2 is an enlarged plan view of the second connector of the present invention (with the inspiratory and expiratory tubes shown in section);

FIG. 2A is a sectional view taken along lines 2A—2A of FIG. 2 (with the inspiratory tube removed);

FIG. 2B is a sectional view taken along lines 2B—2B of FIG. 2A;

FIG. 3A is a sectional view taken along lines 3A—3A of FIG. 1;

V. DETAILED DESCRIPTION OF PREFERRED EMBODIMENTS

Figure 1:
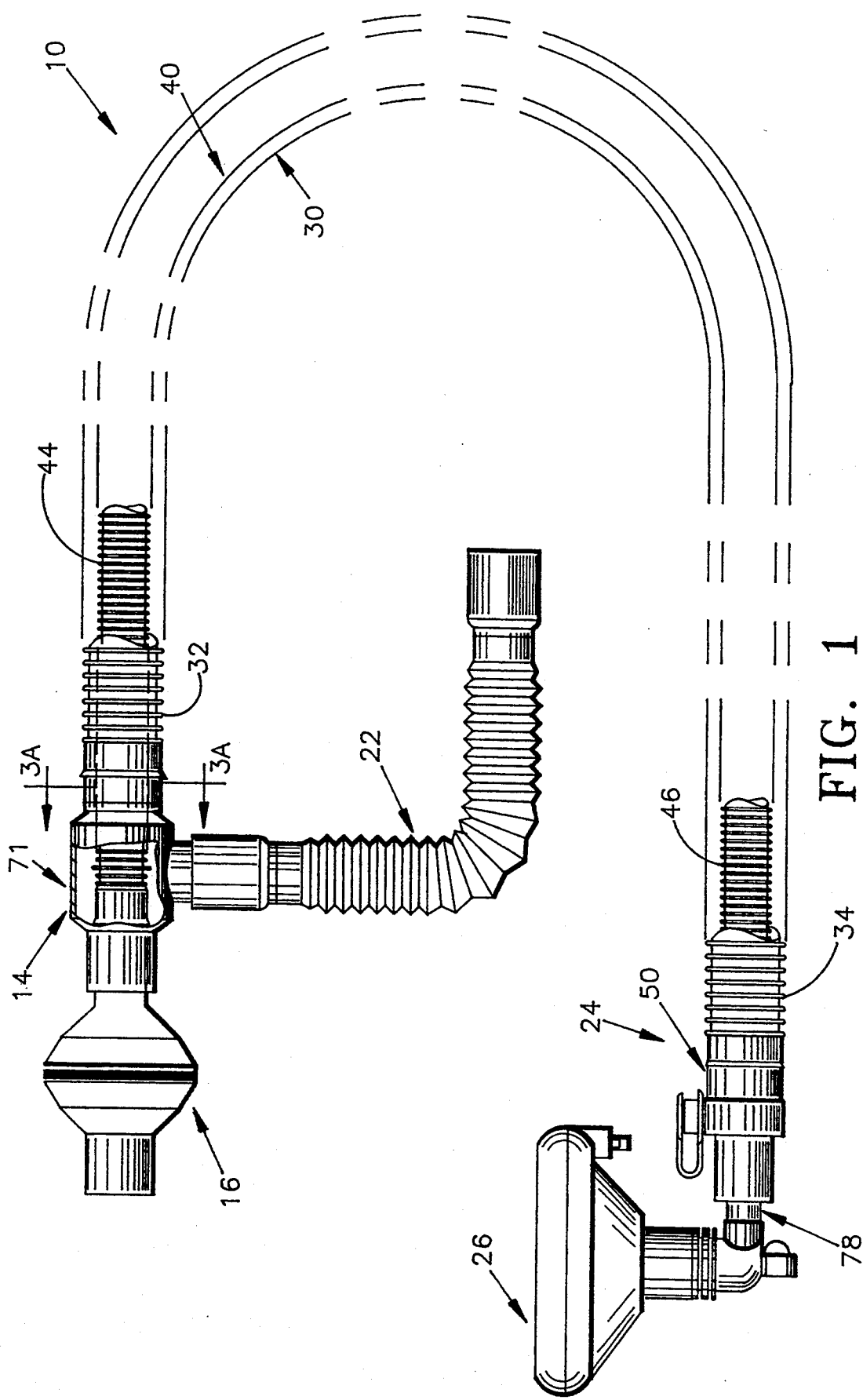
FIG. 1 is a plan view of the breathing circuit of the present invention in its "anesthesia dispensing" mode.

A breathing circuit 10 of the present invention is shown in FIG. 1 which is especially adapted for use in a health care setting. In particular, breathing circuit 10 is adapted for use in connection with the dispensing of an anesthetic to a patient during surgery, and for dispensing a gas such as oxygen or air to a patient after surgery, and later for therapeutic use. The breathing circuit 10 includes a first end 14 which is commonly known as the "machine end" of the device 10. A bacterial filter 16 may be provided which prohibits the transport of bacteria across the filter 16. The downstream end of the bacteria filter 16 is attached to the first end 14 of the device, and the "upstream" end of the bacterial filter 16 is attached to a gas dispensing apparatus. The gas dispensing apparatus typically includes an inspiratory regulator (not shown) for regulating the flow of a gas from a gas storage container such as a tank (not shown) through the breathing circuit 10. An auxiliary expiratory tube 22 extends between the first end 14 of the device and an expiratory regulator (not shown). The expiratory regulator is also part of the gas dispensing apparatus, and controls the flow of expiratory gas.

The breathing circuit 10 also includes a second end 24 which can be attached to a face mask 26, or an endotracheal tube (not shown). Face mask 26 is typically placed over the face of a patient. Several face masks exist that are compatible with the breathing circuit 10 of the present invention, including those face masks manufactured by the assignee of the instant invention, King Systems Corporation of Noblesville, Ind. Also, it should be noted that the second end should be dimensionally compatible with common connectors.

The breathing circuit 10 includes an expiratory tube 30 having a first end 32 disposed at the first end 14 of the device 10, and a second end 34 disposed at the second end 24 of the device 10. The expiratory tube 30 is preferably formed to have a corrugated structure, and is made from a flexible plastic material. One preferred method for manufacturing the corrugated expiratory tube 30 of the present invention is through an extrusion process. Preferably, the expiratory tube 30 has an inner diameter of approximately 1 inch (25.4 mm).

The breathing circuit 10 also includes a corrugated inspiratory tube 40 which is disposed generally colinearly and coaxially, with and interiorally of the expiratory tube 30. The inspiratory tube 40 has a first end 44 disposed adjacent to the first end 32 of the expiratory tube 30, and a second end 46 disposed adjacent to the second end 34 of the expiratory tube 30.

A second end coupling member such as second end connector 50 is provided which is fixedly coupled to second end 34 of the expiratory tube 30, and is configured for loosely, freely, slidably receiving the second end of 46 of the inspiratory tube 40. The second end connector 50 is made from a plastic such as a transparent, clear rigid plastic material. The second connector 50 is best shown in FIGS. 2, 2A and 2B as being generally cylindrical in shape and having a radially outer surface 54 and a radially inner surface 56, a proximal end portion 58 and a distal end portion 60. The radially inner surface of the second end 34 of the expiratory tube 30 is sized for snugly receiving the proximal end portion 58 of the second end connector 50. The snug fit is designed so that during normal use of the breathing circuit 10, the second end 34 of the expiratory tube 30 will not become dislodged from the radially outer surface 54 of the second end connector 50.

The proximal end portion of the radially inner surface 56 of the second end connector 50 functions as a positioning member receiving portion for receiving a positioning member 68 coupled to the second end 46 of the inspiratory tube 40. It includes a series of four axially extending ramps 64 which are formed thereon. The axially extending ramps 64 extend radially inwardly from the radially inner surface 56, such that the effective inner diameter of the interior of the proximal end portion 58 of the second end connector 50 is decreased because of the presence of the ramps 64. The axially extending ramps 64 include radially inwardly facing ramping surfaces 66 which are provided for receiving a positioning member 68. Positioning member 68 is best shown in FIG. 2B as being generally cylindrical in shape, and including an arcuately tapered end 70. One end of the positioning member 68 is inserted into the interior of the second end 46 of the inspiratory tube 40 to be snugly mated to the inspiratory tube 40. During normal use of the breathing circuit 10, the inspiratory tube 40 and positioning member 68 remain joined, and unseparated. The distal end of the positioning member 68 is received by the ramping surfaces 66 of the ramps 64, so that the positioning member 68, and (hence the second end 46 of the inspiratory tube 40) is positioned generally in the center of the interior of the proximal end portion 58 of the second end connector 50.

The ramping surfaces 66 are formed so that the inner diameter of the second connector decreases as one moves in a direction from the proximal end portion 58 to the distal end portion 60. The tapered end 70 of the positioning member 68 and the ramping surfaces 66 cooperate to slidably, freely receive the positioning member 68 on the ramping surfaces 66, so that longitudinal movement of the positioning member 68 on the ramping surfaces 66 is permitted. During use of the breathing circuit 10, it is not unusual for the anesthesiologist to manipulate and distort the circuit in a manner that will adjust the relative longitudinal positions of the second ends 46, 34 of the respective inspiratory tube 40 and expiratory tube 30. When this happens, the positioning member 68 and thus the second end 46 of the inspiratory tube 40 may become disengaged from the ramping surfaces 66 of the ramps 64. When the inspiratory tube 40 is later released, and it and the expiratory tube 30 return to their relaxed positions, the respective shape and configuration of the positioning member 68 and ramping surfaces 66 cooperate to return the positioning member 68 to its proper position on the ramping surfaces 66.

One feature that helps to aid the positioning member 68 in assuming its proper place on the ramping surfaces 66 is the fact that the inspiratory tube 40 has a greater relaxed length than the expiratory tube 30. As the inspiratory tube 40 is trapped between the first end coupling member 71 and the second end coupling member 50, and as the distance between the first end coupling member 71 and second end coupling member 50 is determined generally by the relaxed length of the expiratory tube 30, the effective longitudinal distance that can be occupied by the inspiratory tube 40 is determined largely by the relaxed length of the expiratory tube 30. Because the inspiratory tube 40 has a greater relaxed length than the expiratory tube 30, the inspiratory tube 40, under normal conditions, is not in a relaxed state when assembled into the breathing circuit 10. Rather, the inspiratory tube 40 exerts a longitudinal pressure on the breathing circuit 10. By exerting pressure in a longitudinal direction, the inspiratory tube 40 tends to help push the positioning member 68 toward the distal end portion 60 of the second end coupling member 50 into engagement with the ramping surfaces 66.

The second end coupling member 50 also includes a radially extending monitoring port 72 through which internal gases can be monitored. The radially extending monitoring port 72 is covered by a selectively engageable cap 74. An elbow connector 78 (FIG. 1) is received interiorally in the distal portion 60 of the second end coupling member 50, and couples the second end coupling member 50 to the face mask 26. The elbow connector 78 is provided for permitting movement of the face mask 26 to enable the anesthesiologist to better position the face mask 26 on the face of the patient.

Figure 3:
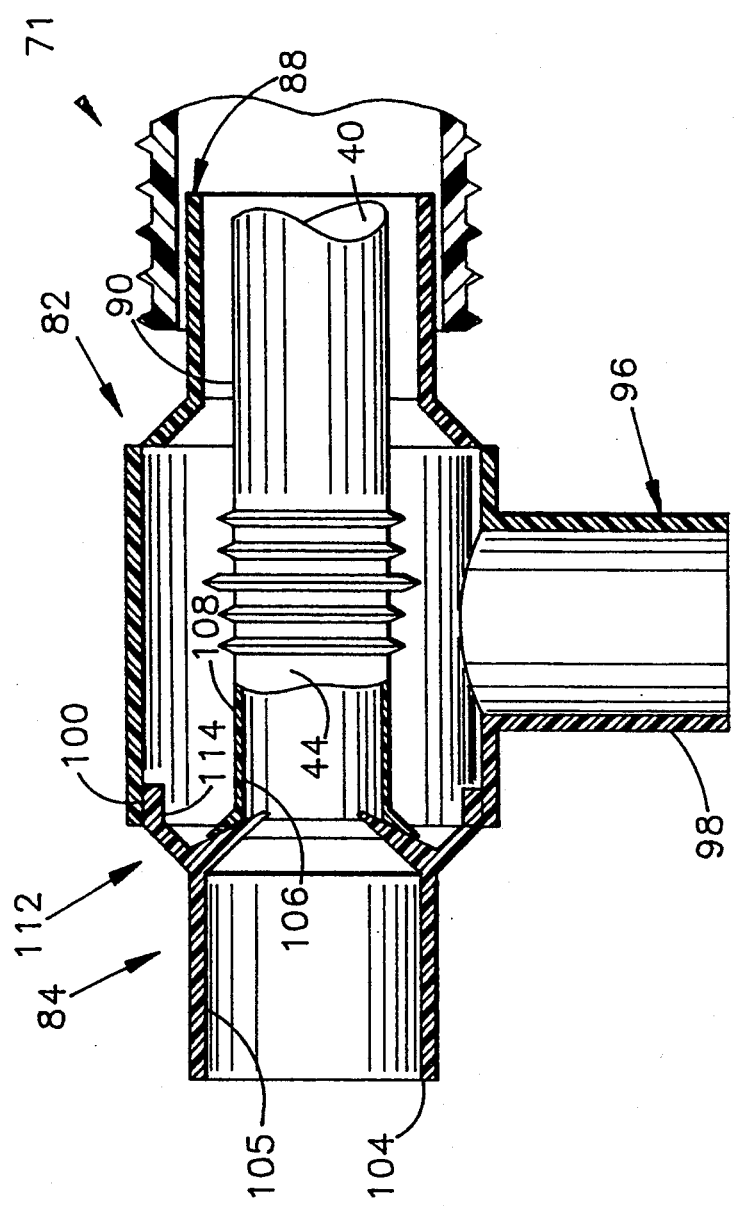
FIG. 3 is an enlarged-sectional view taken along the lines 3—3 of FIG. 4.

The first end coupling member 71 is best shown in FIGS. 3 and 3A. The first end coupling member 71 is preferably formed of a transparent plastic material such as a rigid plastic, and is formed to be generally more rigid than either the inspiratory tube 40 or the expiratory tube 30. The first end coupling member 71 comprises a generally enlarged cylinder having a hollow interior, and an exterior. The first end coupling member 71 includes a first portion 82 which is formed separately from a second portion 84. As will be described in more detail below, the separate first portion 82 and second portion 84 are mated together and then permanently bonded together during the manufacturing process of the breathing circuit 10.

The first portion 82 includes a first, axially extending cylindrical port 88 having a radially outer surface 90. The radially outer surface 90 is provided for snugly engaging the radially interior surface of the first end 32 of the expiratory tube 30. The engagement between the expiratory tube 30 and the first cylindrical port 88 is sufficiently snug so that during the normal useful life of the breathing circuit 10, the first cylindrical port 88 and the expiratory tube 30 do not become disengaged.

The first portion 82 also includes a radially extending third connector port 96. As will be appreciated, the third radially extending connector port 96 is disposed at generally a right angle to the axially extending first cylindrical port 88. The third connector port 96 is in fluid communication with the interior of the first end 32 of the expiratory tube 30, so that gases flowing through the interior of the expiratory tube 30 can pass out of the expiratory tube 30, into the interior of the first end coupling 71, then through and into the third connector port 96. The expiratory gases passing through the third connector port 96 then pass into the auxiliary expiratory tube 22, and ultimately through the expiratory regulator (not shown). The first portion 71 includes a generally cylindrical rim 100 at its proximal end.

The second portion 84 of the first coupling member 71 includes an axially extending second connector port 104 which is disposed generally colinearly with the first connector port 88. The second connector port 104 includes a radially inner surface 105 for receiving a mating connector port of either a bacterial filter 16 or an inspiratory regulator (not shown). The second portion 84 also includes an inspiratory tube connector flange 106 disposed generally colinearly with the second connector port 104. The inspiratory tube connector flange 106 includes a radially outer surface 108 for receiving the first end 44 of the inspiratory tube 40. When the first end 44 of the inspiratory tube 40 is so coupled to the radially outer surface 108 of the inspiratory tube connector flange 106, the interior of the inspiratory tube 40 is in fluid communication with the interior of the second connector port 104, and hence the inspiratory regulator and bacteria filter 16. The connection between the inspiratory tube 40 and the inspiratory tube connector flange 108 is one of the most permanent connections within the breathing circuit 10, as the connection between the inspiratory tube 40 and the inspiratory tube connector flange 108 is the connection that the user would probably least likely desire to become disconnected during use.

The second portion 84 of the first end coupling 71 also includes a first portion connector flange 112. The first portion connector flange 112 includes near its end a generally axially extending circular flange rim 114 which is positioned for snugly engaging the rim 100 of the first portion 82 of the first end coupling member 71. To bond the first portion 82 to the second portion 84, the circular rim 100 of the first portion 82 is placed into engagement with the flange rim 114 of the first portion connector flange 112. The flange rim 114 and rim 100 are then sonically welded to each other along those surfaces at which the flange rim 114 and rim 100 intersect.

The manufacture of the first end coupling member 71 presents a manufacturing challenge. In particular, a manufacturing challenge is faced to find a method for snugly engaging the first end 44 of the inspiratory tube 40 to the radially outer surface 108 of the inspiratory tube connector flange 106. It will be also appreciated that the shape and configuration of the first end coupling member 71 makes it a part that would likely be difficult to mold. To overcome these manufacturing hurdles, the applicants have devised a novel technique for manufacturing the first end coupling member 71.

To manufacture the first end coupling member 71, the first portion 82 is formed separately from the second portion 84. The first portion 82 is first molded to include the first connector port 88 for engaging the first end 32 of the expiratory tube 30. The first portion 82 also includes the third connector port 96 which is placed in fluid communication with the interior of the first end 32 of the expiratory tube 30. The second portion 84 of the first end coupling 71 is then molded to include the second connector port 104, the inspiratory tube connector flange 106, and the first portion connector flange 112, including the flange rim 114. When the first portion 82 and second portion 84 are joined together, the first end 44 of the inspiratory tube 40 is placed over the radially outer surface 108 of the inspiratory tube connector flange 106, and snugly engaged thereto. The inspiratory tube 40 is then passed through the first connector port 88, so that the rim 100 of the first portion 82 will be engaged with the flange rim 114 of the first portion connector flange 112 of the second portion 84. Alternately, the unconnected first portion 82 can be placed over the first end 44 of the inspiratory tube 40 prior to coupling the inspiratory tube 40 to the inspiratory tube connector flange 106. This technique will work so long as the first portion 82 is kept separate and somewhat distant from the inspiratory tube connector flange 106 so that the first end 44 of the inspiratory tube 40 can be manipulated onto the radially outer surface 108 of the inspiratory tube connector flange 106 without interference from the first portion 82.

When rim 100 is engaged to the first portion connector flange 112, the first and second portions 82, 84, are then joined together. Once so joined together, the first portion 82 and second portion 84 are bonded together at the intersection between the rim 100 and the flange rim 114 of the first portion connector flange 112. Although this bonding can be performed with an adhesive such as glue, the applicants have found that the preferred method for bonding together the first portion 82 and second portion 84 is by sonic welding, thus permanently bonding the two together.

One advantage of the present invention is that it is designed to work both in the operating room (in an "anesthesia mode"), and also to be useable with the patient postoperatively during transport from the operating room to the recovery room, used in the recovery room, and also, if necessary be used in the hospital room to which the patient is taken. The breathing circuit 10 of the present invention is best shown in its transport mode in FIG. 4. In the transport mode, the following parts are removed from the breathing circuit: the auxiliary expiratory tube 22, the inspiratory regulator, and the expiratory regulator. Other components are then attached to the breathing circuit 10 in place of the components that are removed. These newly added components include an inspiratory connector 120 which is provided for connecting a gas feed tube 122 to the connector port 104 of the inspiratory tube 40 of the breathing circuit 10. Other newly added components include a breathing bag connector such as expiratory connector 126, and a breathing bag 128.

The inspiratory connector 120 is generally formed from a plastic member sized to be received interiorly by the second connector port 104 of the first end coupling member 71. The opposite end of the inspiratory tube connector 120 is removably engaged to a gas feed tube 122, of the type adapted for connection to an oxygen or air tank. An example of tubing which will function as gas feed tube 122 is tygon-type tubing.

Figure 4:
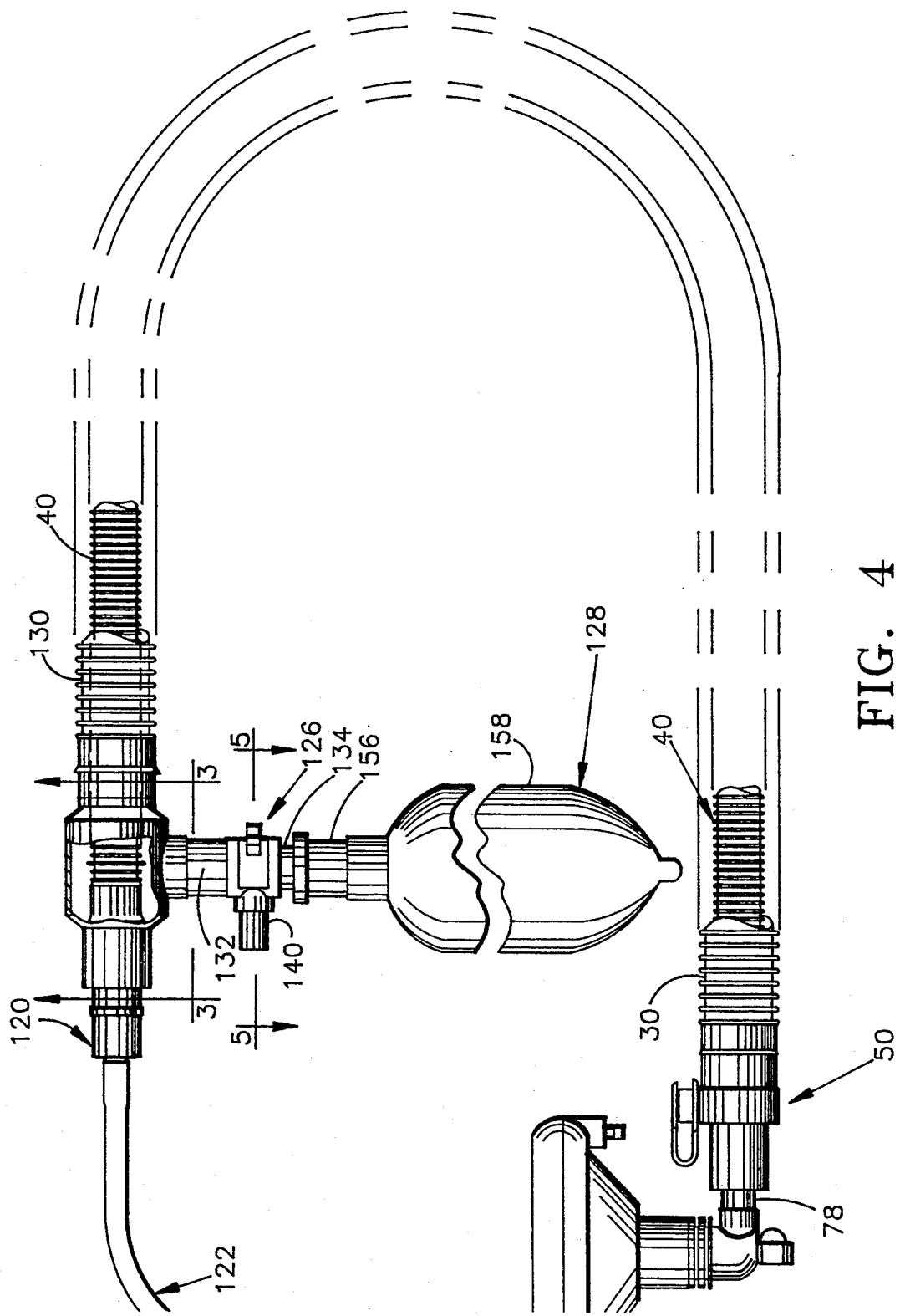
FIG. 4 is plan view of an anesthesia circuit of the present invention shown in its "transport" mode of operation.
Figure 5:
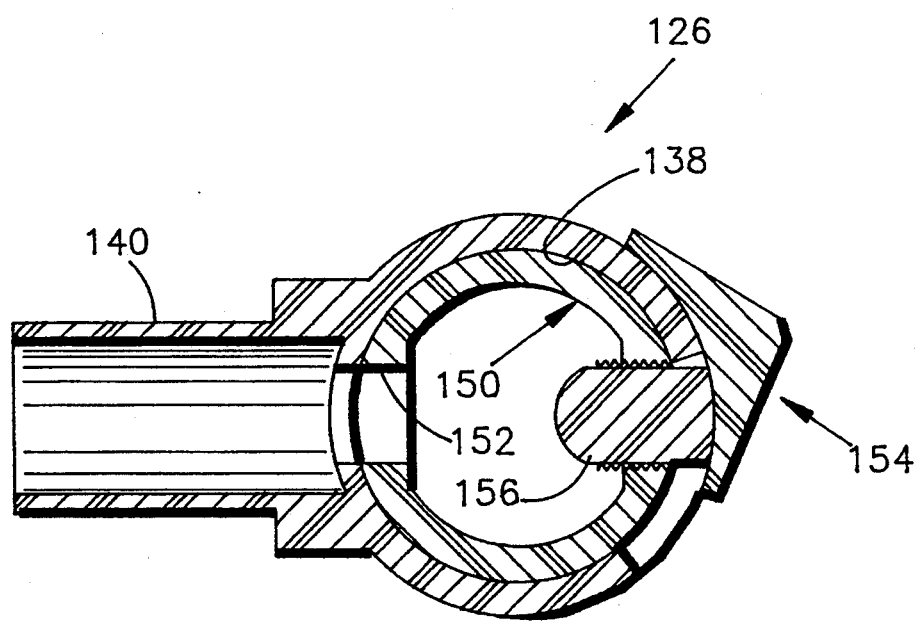
FIG. 5 is an enlarged-sectional view taken along lines 5—5 of FIG. 4.

The expiratory connector 126 is best shown in FIGS. 4 and 5 as including a first axially extending connector port 132, and a second axially extending connector port 134. First connector port 132 and second connector port 134 are generally disposed colinearly. First connector port 132 is sized and configured for receiving the radially outer surface 98 (FIG. 3) of the third connector port 96 of the first end coupling member 71 in a snug engagement. Second connector port 134 is provided for coupling the expiratory connector 126 to the breathing bag 128. The expiratory connector 126 includes a radially inner surface which defines the interior of the expiratory connector 126. The expiratory connector 126 also includes a radially extending exhaust port 140. Exhaust port 140 comprises an aperture formed in the sidewall of the expiratory connector 126, which leads to a generally cylindrical port-type passage.

A valve means is shown in FIG. 5 which is provided for controlling the flow of gases through the exhaust port 140. The valve means comprises a cylindrical ring segment 150 having a radius of curvature only slightly smaller than the radius of curvature of the radially inner surface 138 of the expiratory connector 126. This permits the cylindrical ring segment 150 to fit snugly against the radially inner surface 138 of the expiratory connector 126. The cylindrical ring segment 150 includes an aperture 152 which can be aligned with the aperture of the exhaust port 140. By moving the aperture 152 of the cylindrical ring segment 150 into and out of alignment with the aperture of the exhaust port 140, the flow of gas through the exhaust port 140 can be controlled.

The valve means also includes a knob member 154 which is disposed exteriorly of the expiratory port 126 for actuation by the user's thumb. The knob member 154 is connected to the cylindrical ring segment 150 by a neck 156. Lateral movement of the knob member 154 causes lateral movement of the cylindrical ring segment 150, and hence causes the aperture 150 to move into and out of engagement with the exhaust port 140.

The breathing bag 128 includes a neck portion 156 which is sized to receive the second axially extending connector port 134 of the expiratory connector 126, and a body portion 158. The body portion 158 is preferably made of a stretchable, rubber-like or latex material.

Returning now to FIG. 1, the operation of the device in its anesthesia mode will now be explained. If a bacterial filter 16 is being used, the filter 16 is coupled to the inspiratory regulator 18 and the first coupling member 71 is then coupled to the filter 16. Otherwise, the first coupling member 71 can be coupled to the inspiratory regulator 18. The proximal end of the auxiliary expiratory tube 22 is coupled to the third connector 96 of the first end coupling member 71, and the distal end of the auxiliary expiratory tube 22 is coupled to the expiratory regulator 20. When the user removes the breathing circuit 10 from its packaging, the first connector 71 should already be coupled properly to the expiratory tube 30 and inspiratory tube 40. Further, the expiratory tube 30 and inspiratory tube 40 are already coupled at their second ends to second end coupling member 50. The second end coupling member 50 is then coupled to elbow connector 78 which itself is coupled to face mask 26. During operation, anesthesia gas will flow from its container, through the inspiratory regulator 18, through the bacteria filter 16, and into and through the inspiratory tube 40. Upon leaving the second end 46 of the inspiratory tube, the anesthesia gas will flow through the interior of the second connector, through the elbow connector 78 and into the face mask 26.

It should be noted that prior to the point wherein the inspiratory gas leaves the positioning member 68, the inspiratory gas does not mix with expiratory gas. However, after leaving the arcuately tapered distal end 70 of the positioning member 68, the inspiratory and expiratory gases mix. Although this "dead space" wherein the inspiratory and expiratory gases can mix should preferably be minimized, it may be undesirable to eliminate it entirely.

Expiratory gas is exhaled from the face mask 26, and travels through the elbow connector 78, into the interior of the second end coupling member 50, and then into the space between the inner surface of the expiratory tube 30, and the outer surface of the inspiratory tube 40. The expiratory gas travels along the length of the expiratory tube 30. Upon leaving the first end 32 of the expiratory tube 30, the expiratory gas passes through the interior of the transparent first end coupling member 71, and then travels through the auxiliary expiratory tube 22, and through expiratory regulator 20. The generally enlarged size of the first end coupling member 71, when coupled with its clear plastic transparent composition, enables the practitioner to better monitor the condition of the patient's expiratory gases.

The transition of the breathing circuit 10 from its "anesthesia" mode to the "transport" mode usually occurs at the end of an operation, when the patient is ready for being transported to a recovery room. When this occurs, the auxiliary expiratory tube 22 is disconnected at its coupling with the first end coupling member 71. Additionally, the inspiratory regulator 18 is disconnected from the breathing filter 16, or alternately, the breathing filter 16 is disengaged from the first cylindrical port 84 of the first end coupling member 71.

Turning now to FIG. 4, the inspiratory connector 120 and gas feed tube 122 are then coupled to the first end coupling member 71. Additionally, the expiratory connector 126 and breathing bag 128 are coupled to the third connector port 96 of the first end coupling member 71. When all of this occurs, the device is ready for use in its transport mode, offering the patient a supply of oxygen during transport, and the medical practitioner the ability to manually assist the patient's ventilation..

Having described the invention in detail, with reference to certain preferred embodiments thereof, it will be understood by those skilled in the art that certain variations and modifications exist that are within the scope and spirit of the claims set forth below.

What is claimed is:

1. An anesthesia circuit for conveying an inspiratory gas from a gas dispensing apparatus to a patient, and for carrying an expiratory gas from the patient, the circuit comprising
    (a) a corrugated expiratory tube having a first end and second end,
    (b) a corrugated inspiratory tube disposed generally coaxially and interiorly of the expiratory tube, the inspiratory tube having a first end disposed adjacent to the first end of the expiratory tube, and a second end disposed adjacent to the second end of the expiratory tube,
    (c) a substantially rigid second-end coupling member fixedly attachable to the second end of the expiratory tube, and
    (d) a positioning member fixedly attachable to the second end of the inspiratory tube, for positioning the inspiratory tube relative to the second-end coupling member, the positioning member being relatively more rigid than the inspiratory tube member, wherein the inspiratory tube has a relaxed length sufficiently greater than the relaxed length of the expiratory tube to cause the inspiratory tube to be normally in a partially compressed state to exert longitudinally directed pressure on the second end coupling member, for normally maintaining the positioning member in engagement with the second end coupling member, and the second-end coupling member includes a positioning member receiving portion for freely, slidably receiving the positioning member to permit relative longitudinal movement of the inspiratory tube member and the expiratory tube member, and disengagement and re-engagement of the positioning member and the second end coupling member.

2. The invention of claim 1 wherein the positioning member receiving portion includes a series of axially extending ramps, and the positioning member includes an arcuately tapered end portion to facilitate the free sliding of the positioning member along radially inwardly facing surfaces of the ramps.

3. The invention of claim 1 wherein the first end of the expiratory tube is disposed adjacent the gas dispensing apparatus, and the second end of the expiratory tube is disposed adjacent to the patient.

4. The invention of claim 1 further comprising a transparent, generally hollow first-end coupling member having an interior and an exterior, and being substantially more rigid than the expiratory tube member, the first-end coupling member including:
    (a) a first connector port for engaging the first end of the expiratory tube,
    (b) a second connector port disposed generally colinearly with, and adjacent to the first end of the inspiratory tube, and
    (c) a third connector port in fluid communication with the first end of the expiratory tube.

5. The invention of claim 4 wherein the first end coupling member includes:
    (a) a first portion containing the first and third connector ports, and
    (b) a second portion containing
        (1) the second connector port,
        (2) a radially inwardly flared inspiratory tube connector flange to which the first end of the inspiratory tube is coupled, and
        (3) a radially outwardly flared first portion connector flange being mateable and bondable to the first portion for joining together the first portion and the second portion.

6. The invention of claim 5 wherein the second connector port, the inspiratory tube connector flange, and the first portion connector flange are all disposed coaxially.

7. The invention of claim 4, further comprising
    (a) a breathing bag means,
    (b) a breathing bag connector, the breathing bag connector including a first port adapted to be connected to the third connector port of the first-end coupling member, a second port adapted to be connected to the breathing bag, an exhaust port, and a valve means for controlling the flow of gas through the exhaust port.

8. The invention of claim 7 wherein the means for controlling the flow of gas through the exhaust port comprises a generally cylindrical ring member disposed interiorly of the breathing bag connector, the ring member including an aperture alignable with the exhaust port, and a knob member disposed exteriorly of the breathing bag connector, the knob member being coupled to the ring member for moving the aperture of the ring member into and out of alignment with the exhaust port.

9. A breathing circuit for conveying an inspiratory gas from a gas dispensing apparatus to a patient and for conveying gas from the patient, the circuit comprising:
   (a) a corrugated expiratory tube having a first end and a second end, the expiratory tube having a relaxed length,
   (b) a corrugated inspiratory tube disposed generally coaxially and interiorly of the expiratory tube, the inspiratory tube having a first end disposed adjacent to the first end of the expiratory tube, a second end disposed adjacent to the second end of the expiratory tube,
   (c) a first-end coupling member fixedly coupled to both the inspiratory tube and the expiratory tube, the first end coupling member being generally transparent and hollow, and having an interior and an exterior, the first end coupling member being more rigid than the expiratory tube,
   (d) a second end coupling member fixedly attachable to the second end of the expiratory tube, the second-end coupling member including a positioning member receiving portion, and
   (e) a positioning member for positioning the second end of the inspiratory tube relative to the positioning member receiving portion of the second-end coupling member,
wherein the inspiratory tube has a relaxed length sufficiently greater than the relaxed length of the expiratory tube to cause the inspiratory tube to be normally in a partially compressed state to exert pressure on the second end coupling member, for normally maintaining the positioning member in engagement with the second end coupling member.

10. The invention of claim 9 wherein the positioning member is more rigid than the inspiratory tube member, and includes an arcuately tapered end portion, the positioning member receiving portion includes a series of axially extending ramps, and the positioning member is freely, slidably received on the positioning member receiving portion to permit relative longitudinal movement of the inspiratory tube and the expiratory tube, and disengagement and re-engagement of the positioning member and the second end coupling member.

11. The invention of claim 9 wherein the first-end coupling member includes
   (a) a first connector port for engaging the first end of the expiratory tube,
   (b) a second connector port disposed generally colinearly with, and adjacent to the first end of the inspiratory tube, and
   (c) a third connector port in fluid communicator with the first end of the expiratory tube.

12. The invention of claim 11 wherein the first-end coupling member includes a first portion containing the first and third connector ports, and a second portion, the second portion containing
   (a) the second connector port,
   (b) an inspiratory tube connector flange to which the first end of the inspiratory tube is coupled, and
   (c) a first portion connector flange mateable and bondable to the first portion for joining together the first portion and the second portion.

13. The invention of claim 12 further comprising
   (a) a breathing bag means,
   (b) a breathing bag connector, the breathing bag connector including first port adapted to be connected to the third connector port of the first-end coupling member, a second port adapted to be connected to the breathing bag, an exhaust port, and a valve means for controlling the flow of gas through the exhaust port.

14. The invention of claim 13 wherein the means for controlling the flow of gas through the exhaust port comprises a generally cylindrical ring member disposed interiorly of the breathing bag connector, the ring member including an aperture alignable with the exhaust port, and a knob member disposed exteriorly of the breathing bag connector, the knob member being coupled to the ring member for moving the aperture of the ring member into and out of alignment with the exhaust port.

15. An anesthesia circuit for conveying an inspiratory gas from a gas dispensing apparatus to a patient, and for conveying an expiratory gas from the patient, the circuit comprising
   (a) a corrugated expiratory tube having a first end and a second end, the expiratory tube having a relaxed length,
   (b) a corrugated inspiratory tube disposed generally coaxially and interiorly of the expiratory tube, the inspiratory tube having a first end disposed adjacent to the first end of the expiratory tube, a second end disposed adjacent to the second end of the expiratory tube, and a relaxed length greater than the relaxed length of the expiratory tube such that the inspiratory tube normally exerts longitudinally directed pressure on the circuit,
   (c) a generally hollow, transparent first-end coupling member fixedly coupled to both the inspiratory tube member and the expiratory tube member, the first end coupling member including:
      (1) a first portion containing a first connector port for engaging the first end of the expiratory tube and a third connector port in fluid communication with the first end of the expiratory tube, and
      (2) a second portion containing a second connector port disposed generally colinearly with an adjacent to the first end of the inspiratory tube, the second portion including
         (i) an inspiratory tube connector flange to which the first end of the inspiratory tube is coupled, the inspiratory tube connector flange including a radially inwardly flared portion, and
         (ii) a first portion connector flange mateable with and bondable to the first portion for joining together the first portion and the second portion, the first portion connector flange including a radially outwardly flared portion.

16. The invention of claim 15 further comprising
   (a) a breathing bag means,
   (b) a breathing bag connector, the breathing bag connector including a first port adapted to be connected to the third connector port of the first-end coupling member, a second port adapted to be connected to the breathing bag, an exhaust port, and a valve means for controlling the flow of gas through the exhaust port.

17. An anesthesia circuit for conveying an inspiratory gas from a gas dispensing apparatus to a patient, and for carrying an expiratory gas from the patient, the circuit comprising:
   (a) a corrugated expiratory tube having a first end and a second end,
   (b) a corrugated expiratory tube disposed generally coaxially and interiorly of the expiratory tube, the inspiratory tube having a first end disposed adjacent to the first end of the expiratory tube, and a second end disposed adjacent to the second end of the expiratory tube, (c) a generally hollow first-end coupling member having an interior and an exterior, the first-end coupling member including at least one coupling port, (d) a breathing bag means for holding a gas, and (e) a breathing bag connector, the breathing bag connector including a first port adapted to be connected to at least one coupling port of the first-end coupling member, a second port adapted to be connected to the breathing bag, an exhaust port, and a valve means for controlling the flow of gas through the exhaust port, the valve means comprising a generally cylindrical ring member disposed interiorly of the breathing bag connector, the ring member including an aperture alignable with the exhaust port, and a knob member disposed exteriorly of the breathing bag connector, the knob member being coupled to the ring member for moving the aperture of the ring member into and out of alignment with the exhaust port.

* * * * *

UNITED STATES PATENT AND TRADEMARK OFFICE
CERTIFICATE OF CORRECTION

PATENT NO. : 5,404,873
DATED : Apr. 11, 1995
INVENTOR(S) : Michael A. Leagre; Kevin D. Burrow It is certified that error appears in the above-identified patent and that said Letters Patent is hereby corrected as shown below:

In claim 11, at col. 13, line 51, delete "COMMUNICATOR", and insert therefor--COMMUNICATION--.

In claim 15, at col. 14, line 39, delete "AN", and insert therefor--AND--.

In claim 17, at col. 14, line 66, delete "EXPIRATORY", and insert therefor--INSPIRATORY--.

Signed and Sealed this

First Day of August, 1995

Attest:

BRUCE LEHMAN

*Attesting Officer*  *Commissioner of Patents and Trademarks*

UNITED STATES PATENT AND TRADEMARK OFFICE
Certificate

Patent No. 5,404,873

Patented: April 11, 1995

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Michael A. Leagre, Fishers, Ind.; Kevin D. Burrow, Carmel, Ind.; and Dr. Atsuo F. Fukunaga, Los Angeles, Calif.

Signed and Sealed this Sixth Day of April, 1999.

JOHN G. WEISS
Art Unit 3735